United States Patent [19]

Bricker et al.

[11] 4,312,230
[45] Jan. 26, 1982

[54] METHOD AND APPARATUS FOR PIPE INSPECTION

[75] Inventors: John K. Bricker, Cleveland Heights; Joseph M. Mandula, Jr., Seven Hills, both of Ohio

[73] Assignee: Republic Steel Corporation, Cleveland, Ohio

[21] Appl. No.: 121,814

[22] Filed: Feb. 15, 1980

[51] Int. Cl.³ ............................................. G01N 29/04
[52] U.S. Cl. ..................................................... 73/638
[58] Field of Search ............... 73/622, 625, 628, 633, 73/634, 635, 637, 638, 639, 640, 641

[56] References Cited

U.S. PATENT DOCUMENTS

| | | | |
|---|---|---|---|
| 2,953,017 | 9/1960 | Bincer et al. | 73/640 |
| 3,056,285 | 10/1962 | Gibson et al. | 73/638 |
| 3,077,768 | 2/1963 | Allardt et al. | 73/634 |
| 3,095,501 | 6/1963 | Goekler et al. | 219/124.31 |
| 3,182,490 | 5/1965 | Gibson | 73/638 |
| 3,350,925 | 11/1967 | Coy | 73/638 |
| 3,371,524 | 4/1968 | Wloszek | 73/639 |
| 3,413,843 | 12/1968 | Kortenhoven | 73/638 |
| 3,593,120 | 7/1971 | Mandula, Jr. | 73/635 |
| 3,614,890 | 10/1971 | Bates | 73/634 |
| 3,670,562 | 6/1972 | Muto et al. | 73/634 |
| 4,100,809 | 7/1978 | Bobrov et al. | 73/638 |
| 4,108,004 | 8/1978 | Murakami | 73/638 |

*Primary Examiner*—Stephen A. Kreitman
*Attorney, Agent, or Firm*—Watts, Hoffmann, Fisher & Heinke Co.

[57] ABSTRACT

A mounting system for maintaining a transducer 20 in contact with a pipe 12 during testing. The system is mounted to a frame 32 which is in turn mounted for movement along a length of pipe. A first step in the testing procedure is to position the frame 32 a distance away from the pipe dependent on the pipe diameter. A carriage 34 coupled to the frame is then lowered to a scanning position and scanning takes place as the frame is moved along the pipe. A universal joint mechanism 36 connecting the carriage to the transducer 20 allows up and down and side to side movement of the transducer and thereby allows scanning to continue on pipes with bows and other irregularities along their length. When the pipe end is neared the carriage 34 is retracted away from the pipe 12 by action of a spring mechanism 154. In this retracted position downward movement of the transducer is prevented by a ball support 146, 147 coupled to the transducer and contacting a supporting surface 149 of the carriage. In this way the transducer will not fall from the pipe's end nor collide with the end so that damage to both transducer and mount are avoided.

29 Claims, 18 Drawing Figures

METHOD AND APPARATUS FOR PIPE INSPECTION

DESCRIPTION

1. Technical Field

This invention relates generally to flaw inspection and more particularly relates to a mechanism for maintaining a transducer in contact with a pipe being tested as the pipe and transducer are relatively moved along the entire length of the pipe while limiting relative rotation of the transducer about the pipe's circumference.

2. Background Art

Techniques are known for nondestructive testing of pipe using ultrasonic transducers. In one application the transducer is positioned near a weld area of a pipe. Relative translational movement between pipe and transducer is effected to ultrasonically scan the weld area for flaws and irregularities. One technique for such flaw detection is disclosed in U.S. patent application Ser. No. 933,668, now U.S. Pat. No. 4,195,530, which has been assigned to the Republic Steel Corporation. That application is incorporated herein by reference.

According to the invention disclosed in the referenced application, ultrasonic energy is transmitted to a pipe at equal nonradial angles of incidence. Circuitry is coupled to the ultrasonic transducer for correlating reflections of ultrasonic signals from within the pipe with irregularities in the weld structure of that pipe.

To accomplish the disclosed ultrasonic testing, a detector mounting assembly is utilized with two transducers, each pivotally mounted on either side of the pipe's weld area. According to the disclosed technique the pipe is supported so its weld line is on top. The mouting assembly rests on the pipe and is drawn along its length in a direction parallel to the pipe and as this motion occurs ultrasonic signals are sent from the transducers into the pipe. To achieve and maintain ultrasonic coupling between the pipe and transducer it is necessary to provide a film of water between an ultrasound transmitting surface on the transducer and the pipe. Echo return signals from within the pipe corresponding to flaw locations are then received by the transducers and analyzed by circuitry external to those transducers.

Problems have been experienced in maintaining the ultrasonic transducers in the proper physical relationship to the pipe to be scanned. To properly scan a weld area along the length of a pipe, it is necessary that the ultrasonic transducer remain positioned near that weld area. If the pipe rotates underneath the transducer or if the transducer slips too far around the circumference of the pipe, test results from the transducer echo signals may be in error.

Prior art transducer mounting techniques can cause relative rotation between transducer and pipe. The transducer may provide a torque thereby causing the pipe to rotate or the transducer may slip off the pipe under the action of gravity. In either instance scanning of the weld line is disrupted.

A second disadvantage with prior art transducer mounting schemes is that the transducer is moved away from the pipe as the end of the pipe is neared. This procedure prevents the transducer from falling off the end of the pipe or colliding with the pipe's end. This technique results, however, in no testing of a significant length of the pipe's end portion after the transducer is removed from its ultrasonic test position. In essence, prior art transducer mounting systems fail to maintain transducers in proper relation to the pipe under test for the entire length of the pipe and therefore result in incomplete testing of the pipe under study.

DISCLOSURE OF INVENTION

The present invention overcomes these and other disadvantages in prior art transducer mounting procedures. The method and apparatus featured by the invention provide ultrasonic coupling between a pipe and a transducer along the complete length of the pipe while limiting relative rotation between the pipe and the transducer. The invention has particular applicability to a system for detecting flaws along a weld line of a piece of pipe since that application requires the transducer to be circumferentially positioned within a certain range as the length of pipe is traversed.

A pipe inspection station utilizing the invention includes a support for securing a pipe in an inspection position, an ultrasonic transducer and a mounting for supporting the transducer above the pipe during ultrasonic testing. A drive mechanism provides relative translational movement as the mounting maintains the positioning of the transducer to insure transducer coupling along the entire length of the pipe. As the length of pipe is traversed the mounting also limits the extent of movement of the transducer about the pipe circumference to assure complete scanning of a weld area along the pipe.

In a preferred embodiment of the invention the mounting for the transducer includes a carriage mounted on a frame. The carriage is positioned near a pipe inspection station and movable toward and away from the station. In the preferred embodiment the carriage is directly above the pipe and such movement is therefore in a vertical plane. The transducer is connected to the frame by means of a universal joint mechanism which permits limited transducer movement about the circumference of the pipe. A positioning mechanism, which in the preferred embodiment comprises a spring assembly limits downward movement of the transducer when the end of the pipe is approached.

The frame is movable along the length of pipe and since the carriage and transducer are coupled to the frame, it is longitudinal movement of the frame which causes movement of the transducer along the pipe. The vertical positioning of the frame is also adjustable. Before ultrasonic scanning is initiated the position of the frame is adjusted depending on the pipe diameter. For large diameter pipe the frame is moved up away from the pipe's centerline to position the transducer in proper scanning relation.

Once the frame position has been adjusted, the carriage is moved to a first scanning position and translational movement is initiated. In this first scanning position one or more transducers rest upon the pipe and are coupled to the frame by the universal joint. As translational movement begins the universal joint permits two degrees of translation freedom in transducer movement. In the embodiment wherein the carriage is mounted above the pipe, the universal joint allows up and down and side to side transducer movement.

The testing apparatus shown in U.S. application Ser. No. 933,668 uses two transducers mounted for rotation about an axis parallel with the pipe's centerline. When this transducer mounting scheme is coupled to the universal joint mechanisms the transducers continue to scan the weld area even though pipe irregularities cause the transducer to shift from side to side and up and down.

Sensors are used to sense when the frame nears the end of the pipe. When the pipe end is approached the carriage is partially retracted by the spring assembly to maintain transducer positioning and to prevent the transducer from falling off the end. Were it not for the spring assembly such as undesirable event could occur due to the freedom of movement permitted by the universal joint. In this partially retracted position, however, the carriage in combination with the spring assembly allows ultrasonic testing along an end portion of the pipe.

Relative up and down movement between the carriage and the frame is provided by a pneumatic drive mechanism which is double acting to institute movement of the carriage both toward and away from the pipe. In its normal scanning position the pneumatic drive overcomes the spring force between frame and carriage and drives the carriage to a position where the coupling between transducer and frame is only through the universal joint. To retract the carriage the pneumatic drive initiates reverse upward movement. The spring mechanism continues to retract the carriage and its final position is determined by the coaction between the spring, frame, and carriage.

From the above it is apparent that one object of the invention is to provide a mechanism for mounting a transducer in relation to a pipe for scanning the entire length of the pipe without damage to the transducer or the mounting.

A second object is to cause the transducer to coact with the pipe in such a way that tangential forces applied to the pipe are minimized and so that the transducer does not rotate about the pipe and thereby miss flaws or irregularities in the weld line.

Further objects and features of the invention will become more apparent as the invention is described in detail in conjunction with the accompanying drawings.

BEST MODE FOR CARRYING OUT THE INVENTION

Figure 1:
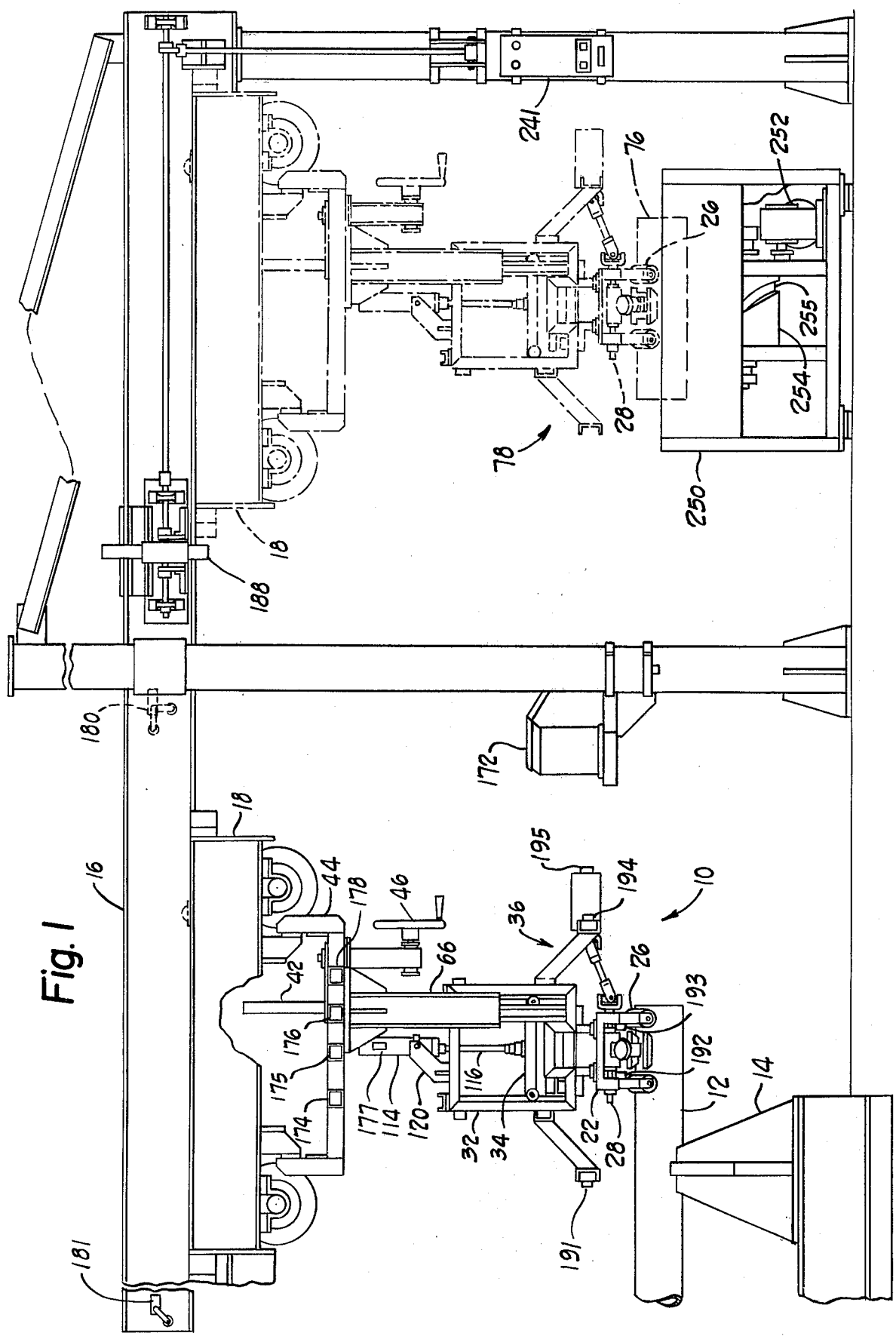
FIG. 1 shows a side elevational view of scanning and calibration apparatus of the present invention and its supporting structure.
Figure 2:
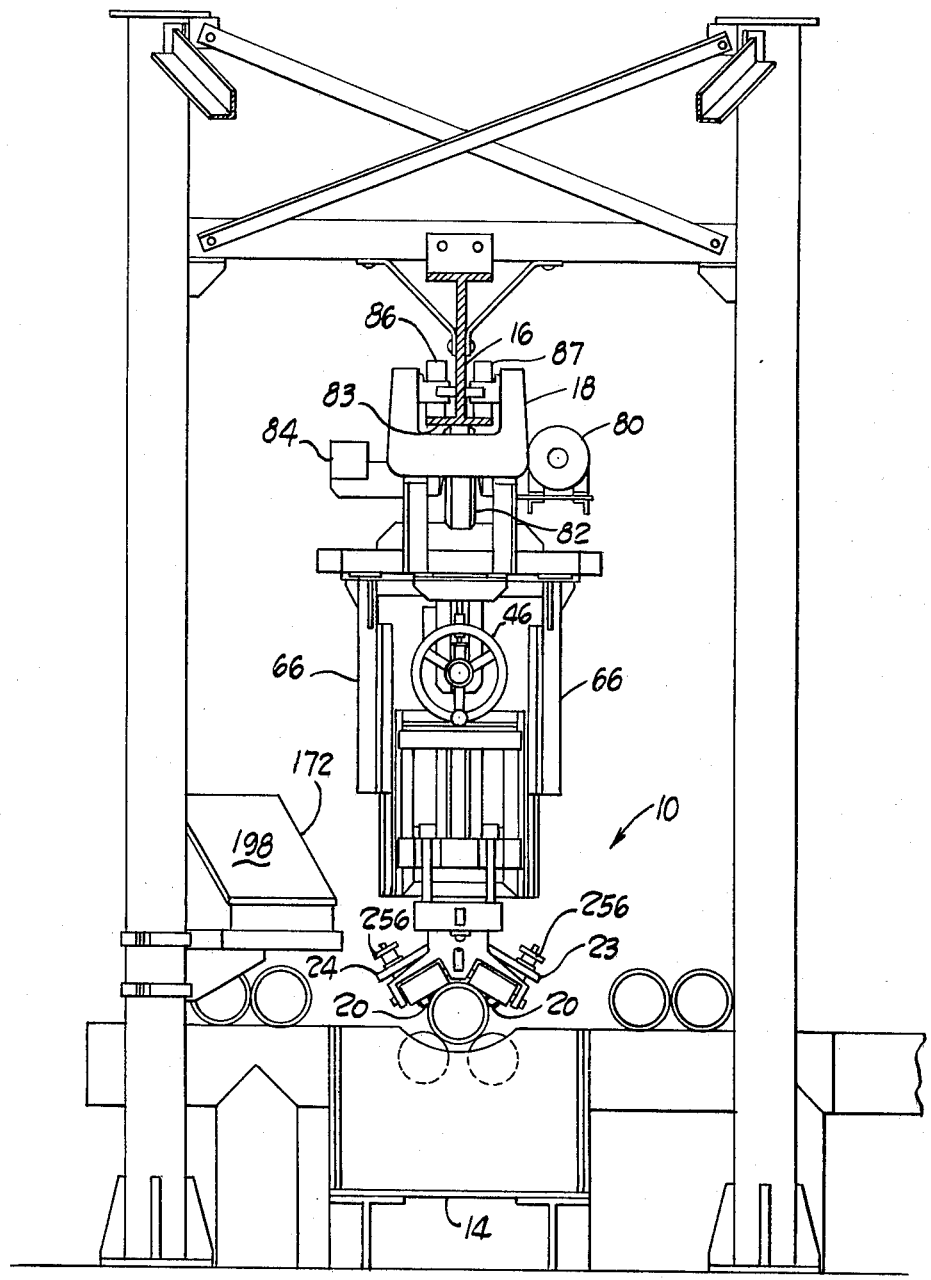
FIG. 2 is an end elevation view of the apparatus and structure shown in FIG. 1.

Referring now to the drawings and in particular FIGS. 1 and 2 there is shown a pipe inspection station or assembly 10 suitable for inspecting a length of pipe 12 for flaws and irregularities. The inspection assembly includes a stand or support 14 for positioning lengths of pipe 12 at an inspection station underneath an I-beam 16. Movably mounted to the I-beam 16 is a trolly 18 which supports scanning apparatus to be moved along the length of the pipe.

As seen in the end view in FIG. 2, lengths of pipe to be inspected are rolled toward the inspection station from the left and positioned underneath the I-beam. Once in position, the pipe is scanned by the scanning apparatus. After the entire pipe length has been tested, the scanning apparatus is moved away and the pipe is rolled from the test station. If many flaws and irregularities are detected within the pipe, it is either marked defective and removed to a scrap area or marked repairable and moved to a repair station. Mechanisms and techniques for moving the pipe toward and away from the test station are known within the art and have been presented only schematically since they form no part of the present invention.

In the embodiment illustrated two transducers 20 (see FIG. 2) are mounted, when in use, at the test station. In this embodiment wherein the apparatus is used for testing a weld line along the pipe's length the transducers are located on opposite sides of that weld line. Under control of electrical circuitry, not shown but discussed in the earlier referenced patent application, ultrasonic signals from both transducers are carefully synchronized to provide ultrasonic scanning of the pipe. Circuitry disclosed in that application carefully monitors the weld area for echo or return signals from that area and controls the marking of defect location within the weld line.

The two transducers are mounted to a test head 22 with two outrigger arms 23, 24 positioned in proximity to the pipe by a number of rollers 26. Both the arms 23, 24 and the rollers 26 are connected to a shaft 28 intermediate the outrigger arms 23, 24 and positioned directly above the weld area. The rollers are free to rotate on the pipe as the test head 22 moves along the pipe length. Rotation between the shaft 28 and the test head 22 is prevented but the arms 23, 24 are free to rotate about the shaft 28 in response to irregularities in shape along the pipe length. Further details regarding the coupling between the transducers 20, the outrigger arms 23, 24, the rollers 26 and the shaft 28 can be found by referring to the earlier referenced patent application, Ser. No. 933,668.

The test head 22 is coupled to the beam-mounted trolley 18 by a mounting mechanism 30. The mounting mechanism 30 (see FIG. 4) comprises a trolley frame 32, a carriage 34, a universal joint mechanism 36 and a wheel adjustment mechanism 38. These elements in combination operate to position the transducers in relation to the pipe and allow movement of the trolley along the pipe's transverse dimension to permit the ultrasonic transducers to scan the entire length of the pipe.

Figure 5:
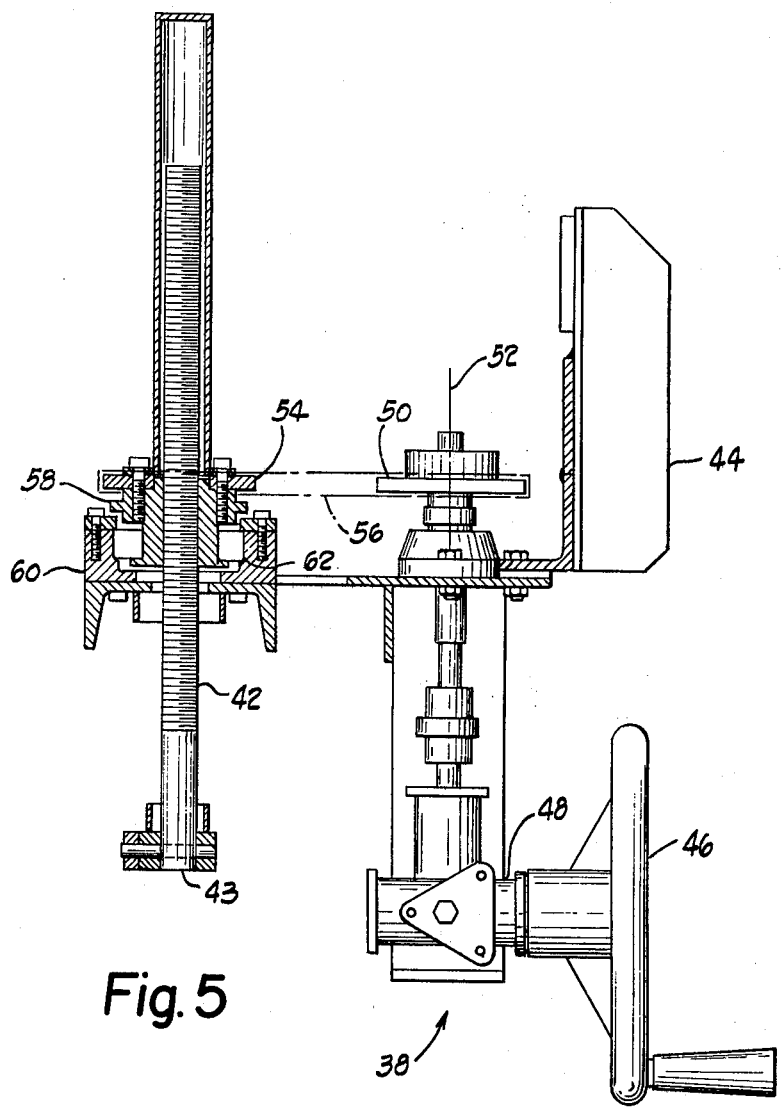
FIG. 5 is an enlarged, partially cross-sectioned view of a wheel adjustment mechanism used to raise and lower a transducer supporting frame.

Rotation of a wheel adjustment mechanism 38 raises and lowers the frame 32 and with it the test head 22. This raising and lowering of the test head is required to accommodate pipe of varying outside diameter. The frame 32 is coupled to the trolley 18 by a threaded shaft 42. As seen in FIG. 5, rotation of the wheel mechanism 38 causes the shaft 42 to raise and lower and since one shaft end 43 is coupled to the frame 32 this movement in turn raises and lowers the frame.

The wheel adjustment mechanism 38 is coupled to the trolley 18 by a mounting bracket 44. This bracket 44 supports a wheel 46, a right angle drive mechanism 48 and a drive sprocket 50. In the preferred and illustrated embodiment of the invention rotation of the wheel 46 causes the drive sprocket 50 to rotate about a vertical axis 52. Since the drive sprocket is coupled to a second sprocket 54 by a chain 56 (shown in phantom in FIG. 5), rotation of the drive sprocket 50 imparts a rotation to the second sprocket 54.

The second sprocket 54 is connected to a bronze nut 58 which coacts with a threaded portion of the threaded shaft 42. Since rotation of the wheel 46 causes the second sprocket 54 to import a rotational motion to the bronze nut, its coaction with the threaded shaft 42 causes up and down movement depending on the direction of rotation of the wheel 46. Thus, the frame 32 can be raised away from or lowered toward the pipe inspection station by rotating the wheel 46.

A second mounting bracket 60 is connected to the trolley 18 and provides support for the bronze nut 58 through a bearing 62. Since the bronze nut 58 through coaction with the threaded shaft 42 supports the frame, it is the connection through this second mounting bracket 60 that supports the frame beneath the trolley and above the pipe inspection station.

Figure 4:
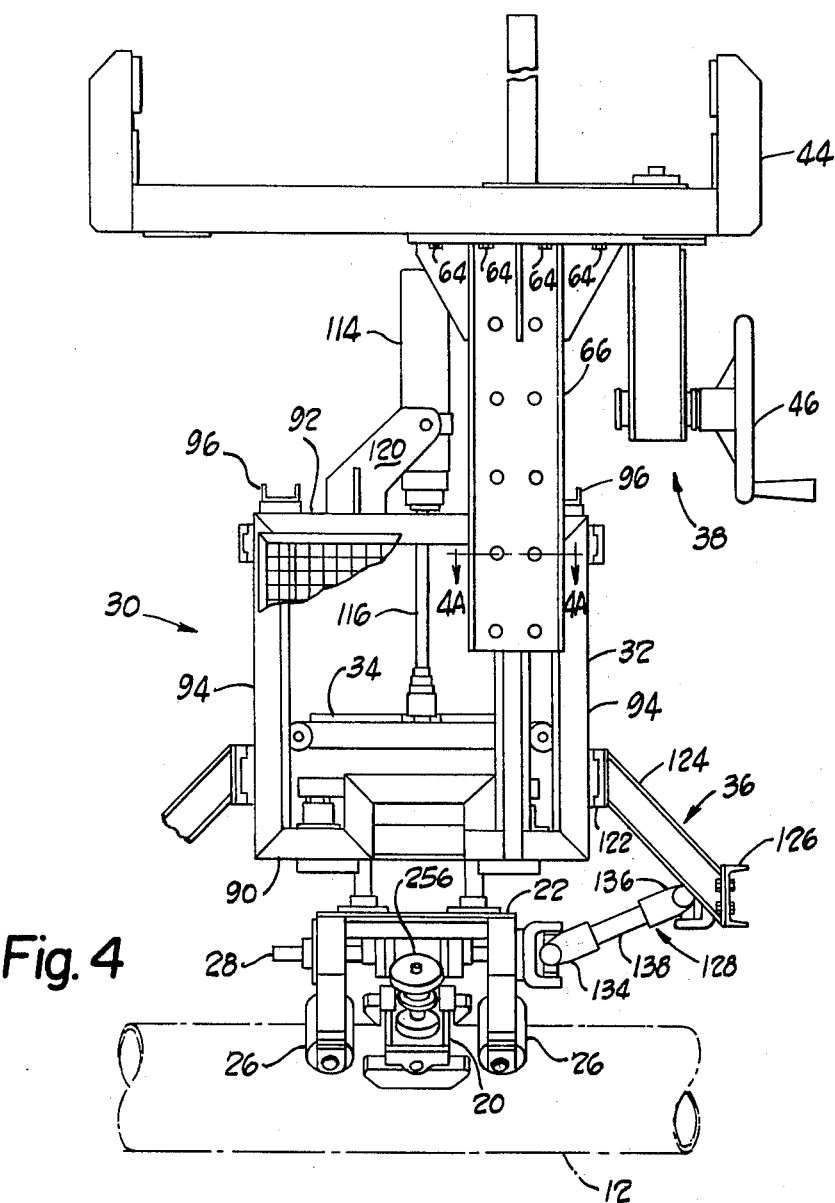
FIG. 4 is an enlarged side elevational view of the scanning apparatus and supporting frame.
Figure 4A:
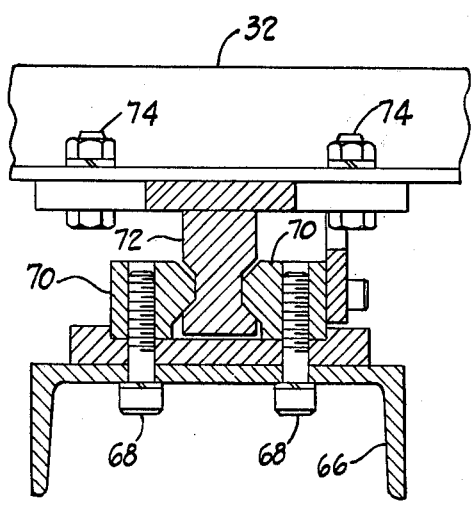
FIG. 4A is an enlarged cross-sectional view as seen from the plane indicated by the line 4A—4A in FIG. 4.

A further coupling between the frame and the trolley is shown in FIGS. 4 and 4A. Coupled to the trolley frame by suitable fasteners 64 are two frame suspension assemblies 66 (both of which are shown in FIG. 2). Coupled to these frame suspension assemblies 66 by other suitable fasteners 68 are guide members 70 which define a pair of channels for a spaced pair of grooved rails 72. Each grooved rail 72 is further coupled to the frame 32 by threaded bolts 74. In this way the suspension frame assembly 66 provides guidance for up and down movement of the frame 32 as the wheel 46 is rotated to cause relative rotation between the bronze nut 58 and the threaded shaft 42.

Before any pipe is tested, the transducers 20 are placed on a segment of calibration pipe 76 which is positioned at a calibration station 78. The segment 76 has the same outside diameter as the pipe to be scanned. During a first step of the scanning process the trolley is moved to a position above the calibration pipe. The wheel 46 is rotated until the two transducers 20 are in an appropriate scanning relationship to the calibration pipe. Once this has been accomplished the vertical positioning of the frame is fixed and not adjusted during testing of a particular diameter pipe. The relative position of the transducers 20 and test head 22 is also adjusted during the calibration procedure and will be described hereinafter. Before the trolley is repositioned over the pipe 12, the carriage 34 is retracted away from the pipe (in a manner to be described) so that the transducers may be safely positioned above that pipe 12.

Movement of the trolley 18 along the beam 16 is achieved by a motor 80 coupled to drive wheel 82 through a suitable drive train, FIG. 2. The motor 80 is mounted on one side of the trolley and therefore a counterweight 84 is positioned on an opposed side of the trolley (see FIG. 2). The drive wheel 82 is positioned underneath and in frictional engagement with a bottom surface 83 of the I-beam 16. The trolley 18 is supported on the I-beam by two support wheels 86, 87 positioned on either side of the I-beam. Energization of the motor 80 imparts a drive to the drive wheel 82 which in turn causes the trolley to traverse the length of the I-beam.

Once the vertical frame position has been adjusted for a particular size pipe and the trolley is positioned above a pipe to be tested, the carriage is lowered and the test head 22 rests on the pipe 12 with the transducers 20 positioned for scanning along the weld line. Once the carriage has been lowered into scanning position coupling between the frame 32 and the transducers 20 is maintained by the universal joint mechanism 36. When the end of the pipe is neared during a pipe inspecting traversed of the transducers 20, in order to prevent the test head 22 and transducers from falling off the end of the pipe the carriage 34 is raised and cables connecting the frame 32 to the carriage 34 help limit transducer movement toward the pipe's axis.

Figure 6:
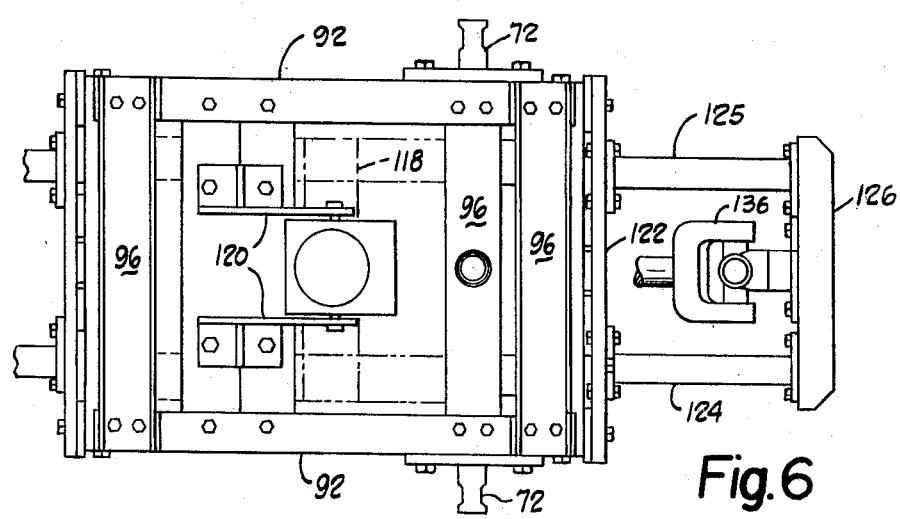
FIG. 6 is a top plan view of the frame of FIG. 5 and an attached universal joint mounting mechanism.
Figure 7:
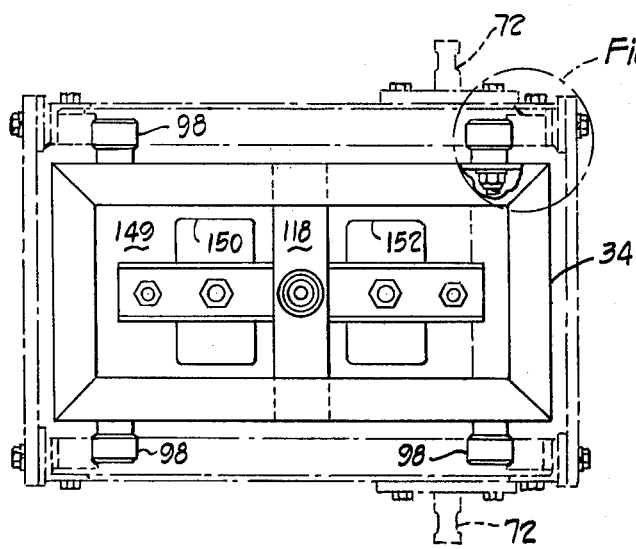
FIG. 7 is a top plan view of a carriage mounted on the frame.
Figure 7A:
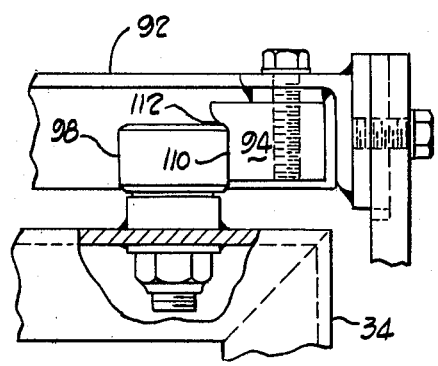
FIG. 7A is an enlarged partially sectioned view showing coaction between the frame and the carriage.

FIGS. 4, 6, and 7 illustrate the mounting and movement of the carriage 34 in relation to the frame 32. The frame 32 is a box-like structure with bottom 90, top 92, side 94 and cross-members 96. The carriage 34 is positioned inside the frame 32 and can move up and down in relation to the pipe 12. The carriage is also box-like and includes eight rollers 98 positioned in contact with the frame's side members 94, (see FIGS. 7 and 7A). Each of the rollers 98 engages an inner surface 110 on the frame side member 94. Each side member 94 includes a restraining lip 112. These restraining lips function to apply thrust loadings to the carriage rollers 98 to limit lateral movement. Thus, the carriage is free to move up and down but not free to move from side to side within the frame.

Up and down movement is imparted to the carriage by a double acting pneumatic cylinder 114 connected to a rod 116. In the preferred embodiment the cylinder 114 comprises a double acting air cylinder Model #10646E manufactured by the Componentrol Corporation. The rod 116 is connected to a crosspiece 118 attached to the carriage 34 and the pneumatic cylinder 114 is connected to the frame by two angled mounting brackets 120. Actuation of the pneumatic cylinder 114 causes up and down carriage movement within the frame 32.

With the rod 116 fully extended and the carriage positioned close to the pipe's outside diameter the primary coupling between the frame 32 and the test head 22 is through the universal joint mechanism 36. One end of this mechanism 36 is connected to a crosspiece 122 (see FIGS. 4 and 6) which extends between two frame side members 94. The other end of the universal joint mechanism is connected to the test head 22.

The universal joint mechanism 36 comprises two rigid universal joint mounting brackets 124, 125, a universal joint support 126, and a universal joint connection 128. The two brackets 124, 125 each extend at an angle down and away from the crosspiece 122 and are connected to the horizontal universal joint support 126. The universal joint connection 128 extends between the support 126 and the test head 22.

Figure 8:
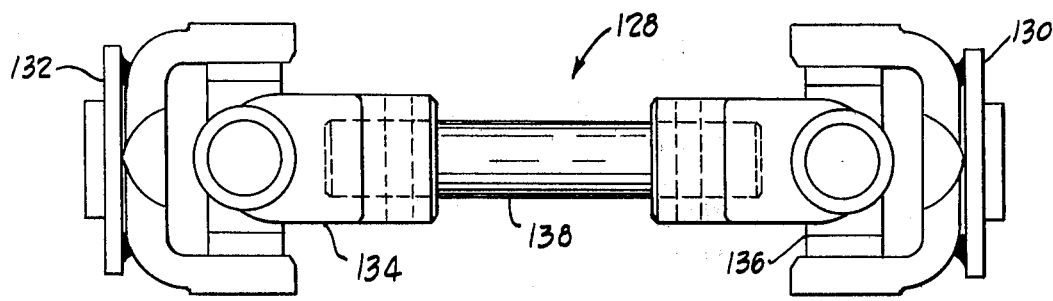
FIG. 8 is a top plan view of a universal joint connection between the frame and a test head.
Figure 9:
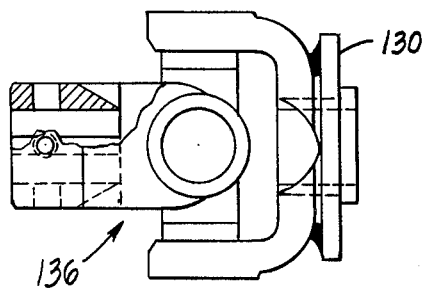
FIG. 9 shows one universal joint used in the universal joint connection of FIG. 8
Figure 9A:
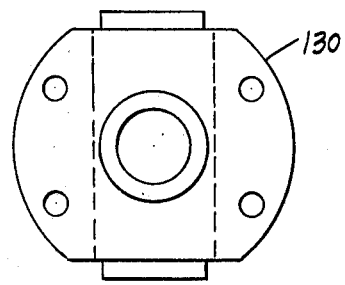
FIG. 9A is an end elevation view of a mounting bracket attached to one end of the universal joint connection.

The universal joint connection 128 (FIGS. 8, 9, and 9A) comprises two supporting brackets 130, 132, two standard universal joints 134, 136 and an intermediate shaft 138. The brackets 130, 132 are identical with each connected by four bolts, the first bracket 130 to the support 126 and the second bracket 132 to the test head 22.

Since the bracket 132 is rigidly connected to the test head 22, rotation of that test head 22 about the pipe's outside diameter is prevented. Thus, the test head 22 is free to move up and down and from side to side due to the universal joint mechanism but it cannot rotate and fall off the pipe's surface. Since the arms 23, 24 which are connected to the transducer, however, are rotatably mounted to the shaft 28, the transducers can be ultrasonically coupled to various diameter pipe.

Coupling between the trolley 18 and test head 22 is through the universal joint mechanism 36 so long as the carriage 34 is fully extended toward the pipe. When the carriage is retracted away from the pipe, however, the test head position and movement is also controlled through a direct coupling between the test head 22 and the carriage 34.

Figures 10, 10A:
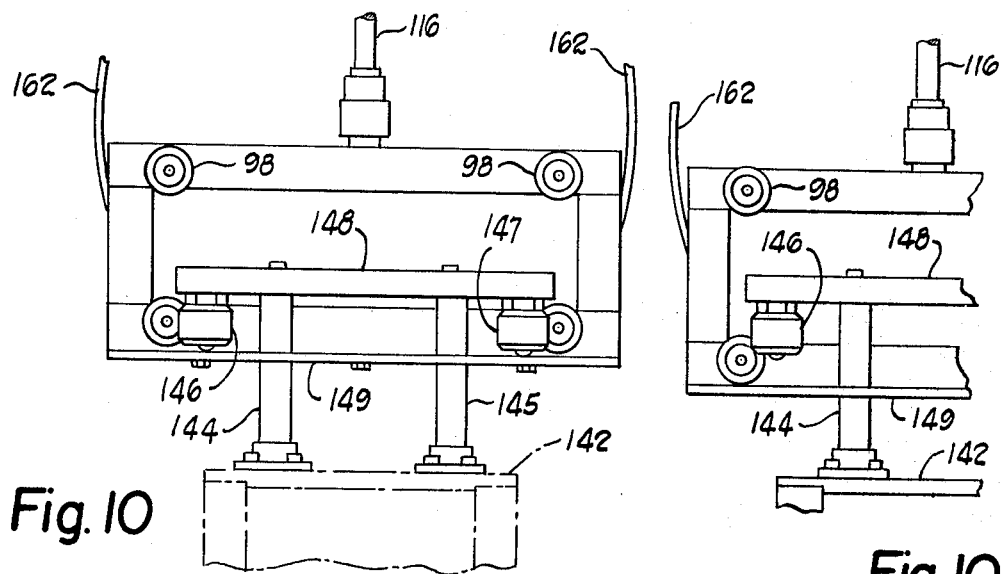
FIG. 10 shows a test head coupled to a carriage surface by a ball joint support.
FIG. 10A shows the carriage of FIG. 10 lowered to a position where the ball joint supports no longer control the carriage surface.

Attached to a top surface 142 on the test head 22 (see FIG. 10) are two vertically oriented cylindrical rods 144, 145. The rods 144, 145 are coupled to two ball transfer supports 146, 147 through a crosspiece 148. When the carriage 34 is elevated away from the pipe the ball transfer supports 146, 147 contact a ball transfer plate 149 connected to the carriage 34. The plate 149 is angled on either side of a centerline to help center the supports 146, 147 above the pipe. The plate 149 defines two apertures 150, 152 (FIG. 7) which limit the extent of allowable side to side movement of the rods 144, 145 and attached test head 22. When the carriage 34 is lowered by the cylinder into its pipe scanning position (see FIG. 10A) with the transducers engaging the pipe 12, the length of the rods 144, 145 supported by the test head 22 is such that the ball transfer supports 146, 147 no longer contact the transfer plate 149.

In an intermediate position when the supports 146, 147 contact the plate 149 coupling between the carriage and the test head allows the transducers 20 to remain in a scanning position as the end of the pipe is neared. In this intermediate position, however, once the end of the pipe is actually reached, the rods 144, 145 and the coacting ball supports prohibit the test head from falling off the pipe 12. The position of the carriage in this intermediate position is dependent on a positioning mechanism 154 mounted to the frame 32 and coupled to the carriage 34.

Figure 11:
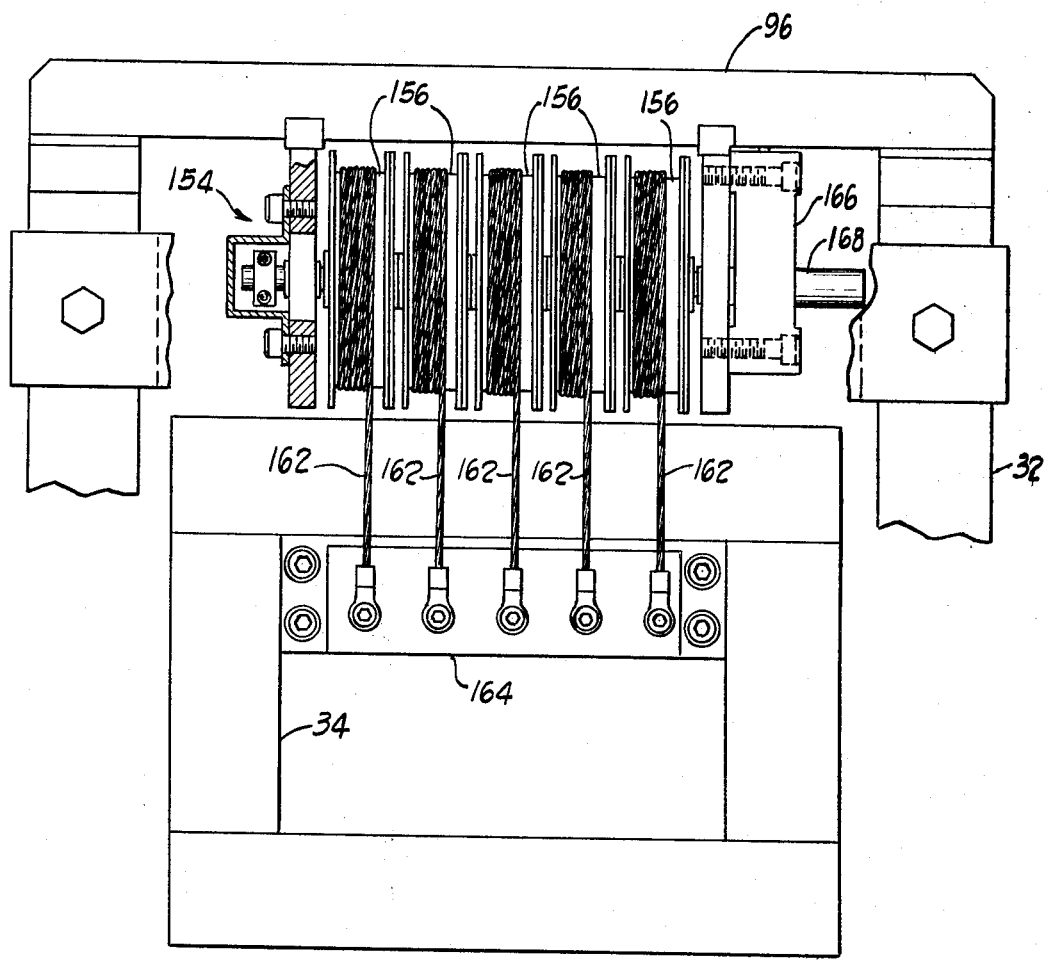
FIG. 11 shows a spring assembly coupling the carriage and the frame to position the carriage in an intermediate scanning position.
Figure 12:
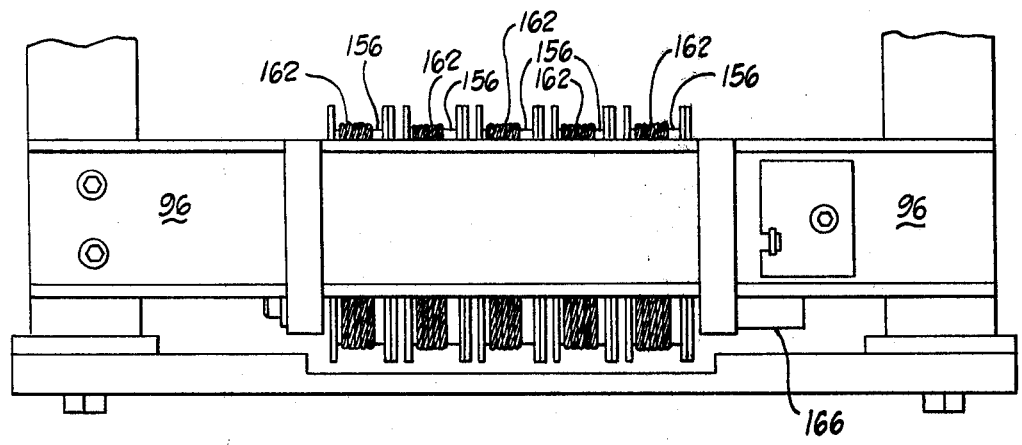
FIG. 12 is a top plan view of a support for the flexible coupling shown in FIG. 11.

In the preferred embodiment of the invention this positioning mechanism 154 (FIG. 11) comprises ten tensioned drums 156 supported from two cross members 96 attached to the frame 32, and a number of cables 162 wound about the drums and connected to two cable mounting brackets 164 on the carriage 34.

Figure 13:
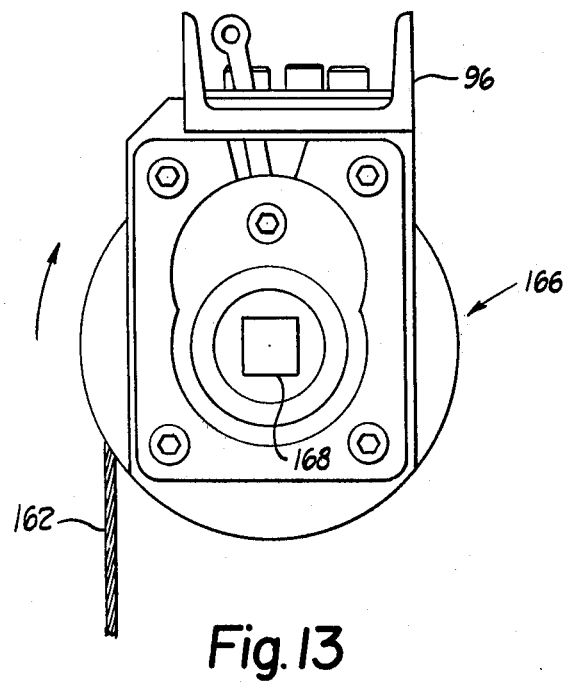
FIG. 13 is an end elevational view of the flexible coupling of FIGS. 11 and 12.

Positioned at one end of each set of five drums 156 is a rachet clutch unit 166. Winding a shaft 168 connected to the rachet 166 in a clockwise direction (FIG. 13) allows the drums 156 to be tensioned to an amount sufficient to raise the carriage above the normal scanning position once the end of the pipe is neared after the pneumatic cylinder 114 is deactivated. In the preferred embodiment the rachet 166 comprises a #71 Lowell rachet clutch unit with $\frac{1}{2}$" square opening and the drums 156 comprise #ML-1912 Hunter (Division of Ametek Inc.) spring powered reels.

The exact position of the carriage at this intermediate scanning position depends on the tension in the spring in the drum assemblies 156 and the weight of the carriage 32. The position must be such that downward movement of the test head 22 is prevented but the transducers 20 remain coupled to the pipe 12. In the intermediate scanning position the transducers remain in scanning contact with the pipe but cannot drop off the end of the pipe due to the coupling between the ball supports 146, 147 and the ball transfer plate. Side to side and upward outrigger frame movement is still allowed by the universal joint mechanism 36 while the extent of such movement is defined by the apertures 150, 152.

To initiate movement of the carriage 34 to this intermediate position from the normal scanning position (i.e. carriage fully extended) the pneumatic cylinder 114 provides a momentary upward thrust to the carriage. The cylinder 114 is then de-activated and the carriage position is dictated by the carriage weight and the tensioning of the reel assembly 156.

Figure 3:
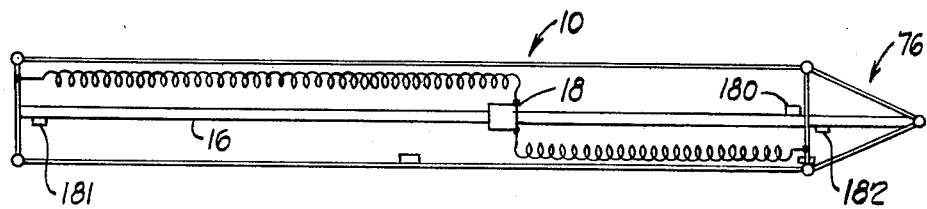
FIG. 3 is a top plan view, on a reduced scale, showing a mounting beam for supporting the scanning apparatus.

The inspection station 10 includes a control console 172 from where an operator may monitor and interact with the station. Circuitry (not shown) interacts with a number of solenoids 174–178, limit switches 180–182, and sensors 191–195 (see FIGS. 1, 2, and 3) to enable the station to operate in both a manual and automatic mode. An exemplary operator control panel 198 positioned on the console 172 is illustrated in FIG. 14.

The panel 198 includes a number of control switches and indicator lamps. The circuitry coupling these controls to the sensors, solenoids and unit switches, does not form a part of the invention and has been omitted from this disclosure. A description of the controls will be provided, however, to allow a better understanding of the scanning features provided by the present invention.

Figure 14:
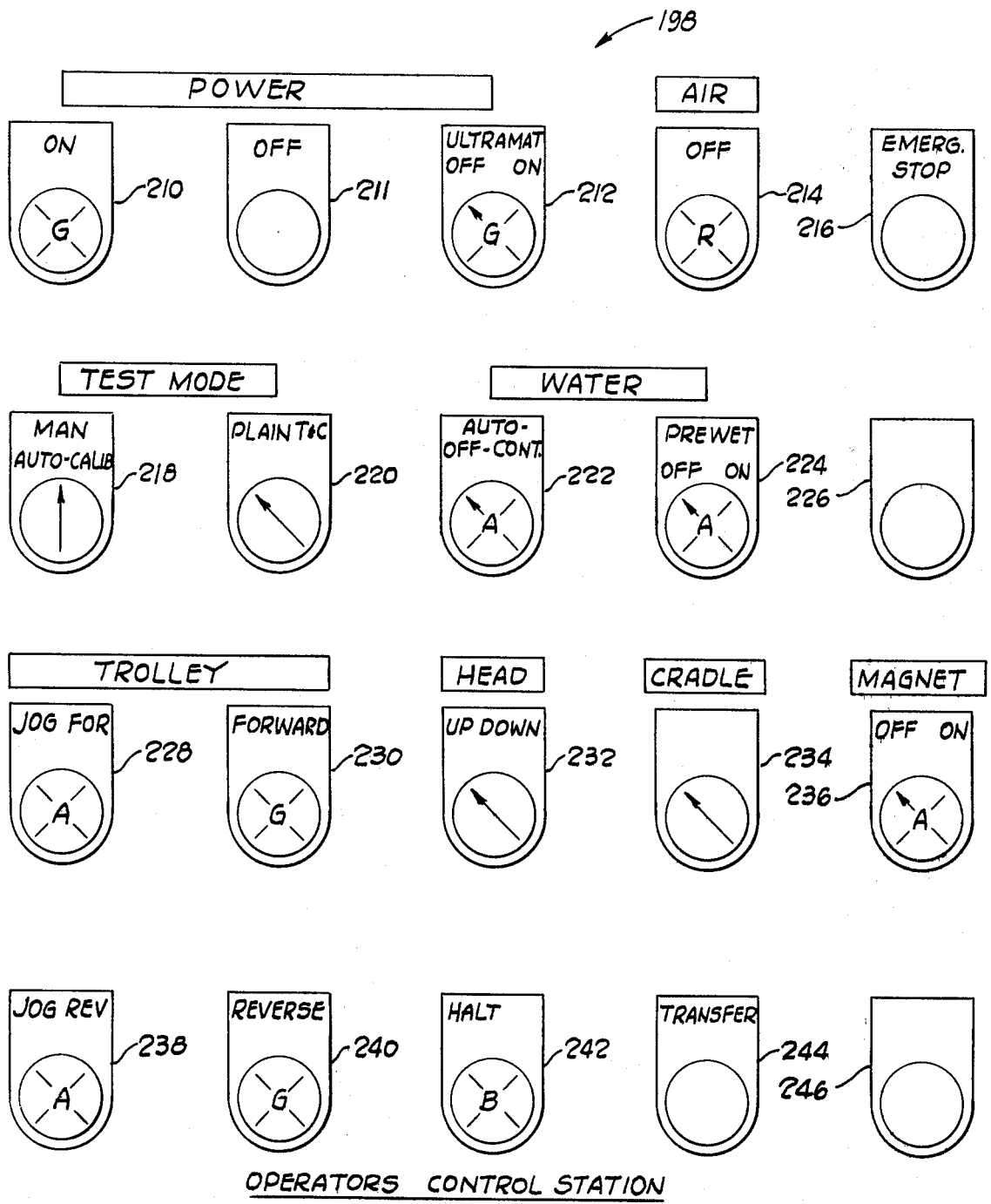
FIG. 14 is a schematic representation of an operator control panel for the inspection systems.

The exemplary switches and indicators are described from top to bottom and from left to right in FIG. 14. A power on 210 and a power off 211 pushbutton control switch controls the electrical power transmitted to the control circuitry. An ultramat power switch 212 controls regulated power to the instrumentation. An air off indicator lamp 214 lights when an air supply coupled to the pneumatic cylinder is off. An emergency stop switch 216 terminates electrical power to the system. When this switch is activated all equipment comprising the inspection station will stop moving.

The inspection station 10 can be operated in either an automatic or a manual test mode. Activation of two test mode switches 218, 220 dictate which of these modes is to be used. In the automatic mode, movement of the transducers is automatically controlled to scan an entire length of pipe. In the manual control mode each control must be individually selected. A calibration selection position on the manual mode switch 218 permits the trolley to be driven past an east end extreme travel limit switch 180 to the calibration station 78.

The inspection station is capable of scanning both plain and threaded and coupled pipe. If plain end pipe is to be examined the test mode selector switch 220 is set to a "plain" position. If threaded and coupled pipe is to be inspected, the test mode selector switch is set to the "TNC" position.

A water selector switch 222 controls the operation of three water solenoids 174, 175, 176 which supply water to the ultrasonic transducers and to a prewet nozzle. When the water selector switch 222 is set in an "auto position" water to the transducers is controlled by positioning of the transducers and is automatically turned off when the carriage is retraced. A so-called prewet operation is also controlled when a prewet switch 224 is in an on position. In a "cont" position, water is continuously supplied to both transducers and the prewet nozzles and the position of the prewet selector switch does not affect this operation.

A transfer push button 244 causes transfer arms (not shown) to move a pipe from a test position to a storage rack and also causes a next pipe to be moved into a test position. Transfer can only be accomplished when the test head 22 has been removed except when the test mode switch 218 is in a calibration selection mode. When a pipe is transferred into a test position, a pipe rotate drive (not shown) is used to position the pipe weld to the top of the pipe length. A magnet select switch 236 is then set to an on position to clamp the pipe in a proper testing position. Once testing has been completed the magnet is switched off and the transfer pushbutton is then pressed to discharge the tested pipe and position a new pipe within the test station. When the system is operating in an automatic cycle the magnet on and off switch is automatically operated. A cradle selector switch 234 controls movable cradle arms to accept a defective pipe adjacent the inspection station.

The trolley functioning is controlled by a series of switches labeled with reference numerals 228, 230, 238, and 240. A jog forward and jog reverse 228, 238 pushbutton control switches cause the test head trolley to move either forward or backward at low speeds as long as an appropriate jog pushbutton is depressed or until an extreme travel limit switch 180 or 181 is actuated. A second set of jog buttons are located on the test head assembly and function in the same manner as these jog forward and jog reverse switches. A third set of jog pushbuttons are located at a calibration drive control 241 (see FIG. 1) and function as described but are only operative when the test mode selector switch is in the calibration position 76.

The forward and reverse switches 230, 240 cause the test head trolley to move at high speeds in a designated direction until a halt scan pushbutton 242 is pressed or alternatively until an extreme travel limit switch is actuated. The halt scan pushbutton 242 stops the travel of the trolley when it is pressed.

Raising and lowering of the transducers is controlled by a test head movement switch 232. This switch controls the raising and lowering of the test head by controlling a test head raise and lower solenoid 178. The switch 232 is operated by selecting the desired function (i.e. either up or down) and then pressing a pushbutton switch.

The following numbered steps are to be performed during a preliminary setup stage before the apparatus can be calibrated and scanning begun.

1. The main supplies for electrical power, air and water are "ON".
2. Pipe 12 to be inspected is on the table ahead of the Test Station 10.
3. The selector switches on the Operators Control Panel 198 are set as follows:

Ultramat Power 212: OFF
Test Mode 218: CALIB
Test Mode 220: PLAIN
Test Head 232: UP
Test Head Water 222: OFF
Prewet Water: OFF
Magnet 236: OFF
Cradle 234: CLOSE 4. Push "Power On" pushbutton 210 to energize control.
5. Set Ultramat Power switch 212 to "On".
6. Press the Test Head pushbutton 232.
7. Set Test Head Water switch to "on".
8. Set Prewet Water switch as desired.

Once these preliminary setup steps have been performed the station 10 is ready for calibration. During the calibration procedure the positioning of the frame 32 is adjusted for the particular diameter pipe to be examined. As a first step, the test mode selector switch 218 is set to the position labeled "calibrate". This step is performed before a mechanical trolley stop 188 on the support beam 16 is manually retracted to permit the trolley to travel to the calibration position. While the trolley mechanical stop 188 is manually retracted, the jog reverse pushbutton is activated and causes the trolley to move to the calibration position. Once the trolley is in calibration position the mechanical stop 188 is engaged and trolley movement thereby prevented.

The calibration station 78 comprises a stand 250 for supporting the calibration pipe 76 beneath the test head 22 when the trolley is in this locked position. To scan pipe of a particular outside diameter the vertical position of the frame 32 must be adjusted and the relative positioning of the transducers in relation to the test head is varied.

As discussed above the vertical position of the frame 32 is adjusted by rotating the handle 46 to either raise or lower the frame. To facilitate proper frame positioning a series of marks calibrated in units of pipe diameter have been made on the frame. A stationary pointer attached to the frame suspension assembly 66 is aligned with an appropriate one of the markings and allows the user to quickly position the frame 32 for a particular diameter pipe.

The calibration pipe 76 has a weldline with artificially introduced flaws at locations along the weldline. With the frame properly adjusted the test head is lowered onto the pipe and the test pipe 76 is scanned so that the position of the transducers 20 in relation to the pipe weld may be adjusted.

To position the transducers 20 the calibration pipe 76 is reciprocated beneath the test head by a motor 252 coupled to a cam 254 having a cam slot 255. The pipe 76 is scanned and return or echo signals received by the transducer 20 are viewed on an oscilliscope until those signals produce maximum flaw indications for the artificially introduced flaws. The transducer position is then fixed by tightening two hold down handles 256 which coact with two threaded studs attached to the two transducers 20. When tightened the handles 256 frictionally engage a transducer mounting bracket to prevent transverse transducer movement either toward or away from the test head 22.

Once calibration has been achieved the mechanical stop 188 is again manually retracted and the trolley is caused to move in an opposed direction by the jog forward pushbutton 228. The apparatus is then ready for operation in either the manual or automatic mode of ultrasonic scan testing.

During a first step in manual mode scanning the operator loads a pipe into the inspection station by pressing the transfer button 244 on the control counsel 172. This causes a pipe to be positioned under the I-beam for untrasonic scanning. The pipe is rotated into a weld line up position and clamped in place by actuating the magnet 236 switched to an on position. The test head is then moved to a desired position above the pipe by operating the jog forward 228 or the forward 230 pushbuttons.

Once the test head is positioned above the pipe it is lowered onto the pipe by moving the test head selector switch 232 to the "down" position and pressing the pushbutton. After coupling water has been established between the pipe and the transducer the trolley is moved as desired along the pipe length. If the pipe end is sensed by an end sensor the trolley will automatically stop. The test head selector switch must then be set to the "up" position and the button pressed to raise the test head before further movement can be accomplished. Once testing is completed the test head is raised and the trolley may be positioned away from the pipe. The magnet fixing the pipe in position is turned off and the scanned pipe is removed from the test station.

In the automatic mode of operation the preliminary steps are identical to the manual mode. Once these steps have been completed, however, the test mode selector switch 218 is then switched to the "automatic" position and the test mode switch 220 set for a particular type of pipe to be scanned. If threaded and coupled pipe is scanned the test mode selector is switched to the "T & C" position. The pipe is loaded into the inspection station by pressing the transfer button 244 and the pipe is rotated to a weld line up position.

To initiate automatic operation of the testing apparatus the operator presses the "forward" pushbutton which causes the magnet to clamp the pipe as the trolley begins moving forward at high speed with the test head up. When the pipe end is sensed by a first sensor 191 the trolley speed is automatically reduced to a low range. When a second sensor 195 senses the end of the pipe the trolley travel is stopped and the test head is lowered on to the pipe as water for coupling is turned on. The test head 22 is now ready to begin scanning the weld line along the length of the pipe.

Once two sensors 192, 193 sense the pipe as the test head 22 is lowered the trolley moves in a reverse direction at low speed until the sensor 195 senses the end of the pipe. Once this occurs the trolley travel is changed to a forward direction at high speed and the trolley travels along the length of the pipe until sensor 191 senses the extreme end of that pipe. Then the test head is raised and trolley travel is stopped as the water is turned off and the magnet is deenergized. The scanned pipe is removed from the test station and a second pipe is loaded into the test position.

Since the unit is now testing threaded and coupled pipe the intermediate position for the carriage above the test head is not used because the extreme end of the pipe includes a coupling. When a second pipe is positioned in the test station the operator presses the reverse 240 pushbutton to start the automatic testing in an opposite direction. This process continues as long as there is pipe to be tested. The operator presses first the forward and then the reverse pushbutton to begin testing in a given direction. Automatic scanning in this mode can be accomplished regardless of the initial position of the test head above the pipe. The sensors on board the scanning apparatus serve to reposition the test head in relation to the end of the pipe before high speed scanning is conducted.

For plain end pipe all the necessary preliminary steps are performed and again the test mode selector switch 218 is set to "automatic" position. Next the test mode selector switch 220 is set to "plain" position and pipe is loaded into the inspection station by pressing the transfer 244 button. Once the pipe has been rotated to the weld line up position the operator presses the forward pushbutton 230 to initiate automatic scanning operation.

This step causes the magnet to energize and clamp the pipe in position and the trolley to move at high speed with the test head up. The pipe end is sensed by a first sensor 191 and the trolley speed is reduced to a low range. When the pipe end is next sensed by a second sensor 194 the trolley travel is stopped and the test head is lowered onto the pipe by energization of a test head lower solenoid 174 with the water turned on. When sensors 192, 193 sense the pipe, trolley travel is begun in a reverse direction at low speeds until sensor 194 senses the pipe end at which time the test head lower solenoid 174 is deenergized. This denergization in combination with energization of a test head float solenoid 175 causes the test head 22 to first rise under action of the air cylinder and then to float on the tensioned drum 156 which couples the frame 32 to the carriage 34. When a sensor 193 senses the pipe end the trolley travel is then reversed and the trolley moves forward at low speed. When sensor 194 passes the pipe end the test head lower solenoid 174 is again energized causing the carriage to extend to its full length and the trolley travel is increased to high speed. During this high speed scanning the coupling between frame and test head is through the universal joint and not through the ball transfer mechanism.

Once the trolley has traveled to the opposite end of the pipe, sensor 191 senses the pipe and and the test head lower solenoid 174 is again deenergized causing the test head to float on the tensioned drum 156. Also at this step the trolley speed is reduced to low speed. When sensor 193 senses the pipe end the entire pipe length has been scanned and a test head raise solenoid 178 is energized. This causes the test head to rise off the pipe and trolley travel is again stopped. The water is shut off and the magnet positioning the pipe is deenergized. Another pipe is loaded into the test station and the reverse pushbutton 240 is pressed to again begin automatic scanning of the plain ended pipe.

Should the sensors 191-195 malfunction two limit switches 180, 181 (See FIG. 3) sense trolley movement and terminate motion. Thus, if an extreme sensor 191 malfunctions as the trolley is moving forward a west end limit switch 181 will contact the trolley and movement will be terminated. The east end limit switch 180 functions in a similar manner for backward movement.

It should be noted that any time the switch 218 is set for automatic scanning, either for plain or threaded a coupled pipe, it is possible to push the halt scan pushbutton 242 and the trolley travel at that time will stop. The jog forward 228 or jog reverse 238 pushbutton can then be used to move the test head as desired along the pipe. Once the automatic scan cycle is restarted by pressing forward 238 or reverse 240 pushbuttons automatic scanning again continues as described above.

From the above discussion it should be appreciated that interaction between the sensors mounted to the test head and the energizing and deenergizing of the solenoids produces automatic scanning whereby the transducers and accompanying test head are prevented from falling off the end of the pipe as the pipe end is neared. Signals from the sensors 191–195 cause the carriage to automatically rise through coupling to the tension drums 156 when the pipe end is neared. In this position the ball supports 146, 147 prevent test head movement toward the pipe center. It should also be appreciated that during fast movement scanning away from the pipe ends the ball supports 146, 147 ride above the plate 149 and therefore coupling between the frame and the test head is through the universal joint mechanism 36.

While the present invention has been described with particularity, it should be appreciated that various modifications and alterations, particularly in the control of the scanning function may be made without departing from the spirit or scope of the invention set forth in the appended claims.

We claim:

1. A pipe inspection system comprising:
    (a) support means for positioning a pipe at an inspection station;
    (b) an ultrasonic transducer for examining the pipe for defects;
    (c) mounting apparatus including a frame and coupling structure connected between the transducer and the frame for positioning the transducer in relation to the pipe;
    (d) drive means for providing relative longitudinal movement between the transducer and the pipe; and (e) said coupling structure including structure for facilitating relatively flexible transducer tracking of undulations along the pipe surface for maintaining ultrasonic coupling between the pipe and transducer during said relative movement along the length of the pipe while substantially preventing movement of the transducer about the pipe circumference.

2. The apparatus of claim 1 wherein the mounting apparatus comprises:
    (a) said frame being positioned near the pipe and movable in a direction perpendicular to the path of pipe travel;
    (b) a test head mechanism coupled to the frame and positionable on the pipe; said test head coupled to the transducer;
    (c) universal joint means connected to said test head for limiting test head translational movement with respect to the pipe axis to substantially two degrees of translational movement; and
    (d) positioning means connected to the frame and couplable to the test head for impeding movement of the transducer in a vertical direction as the transducer nears the pipe end.

3. The apparatus of claim 2 which further comprises a carriage means supported within the frame for vertical movement relative to the frame and couplable to the test head; said positioning means connected between the frame and carriage means and operative to position said carriage with the frame during selected intervals of pipe testing.

4. The apparatus of claim 3 which further comprises a pneumatic cylinder connecting the frame to the carriage to provide vertical movement to the carriage.

5. The apparatus of claim 4 which further comprises ball support means connected to the test head and positioned to contact a surface of the carriage means when the carriage means is moved away from the pipe by combined action of the positioning means and the pneumatic cylinder.

6. The apparatus of claim 4 which further comprises sensor means for sensing the position of the transducer along the pipe and for actuating the cylinder in response to said sensing.

7. A mounting system for maintaining a transducer in contact with a pipe during testing comprising:
    (a) a frame mounted for movement along the pipe;
    (b) means for adjusting the distance of the frame from the pipe;
    (c) a carriage pneumatically coupled to the frame for movement toward and away from the pipe;
    (d) coupling means connected to the transducer for constraining radial movement between the transducer and the carriage when the carriage is in a retracted position; and
    (e) positioning means connected to the frame and to the carriage to locate the carriage in said retracted position.

8. The apparatus of claim 7 wherein the frame is positioned above the pipe and the coupling means supports the transducer when the carriage moves away from the pipe.

9. A method for maintaining a transducer in contact with a pipe comprising the steps of:
    (a) positioning a pipe in relation to a frame, said frame movable along the length of the pipe;
    (b) connecting a transducer to the frame with a universal joint mechanism spaced from the transducer which restricts transducer translational movement with respect to the pipe to substantially two directions orthogonal perpendicular to frame movement direction while said transducer rests on the pipe; and
    (c) providing relative longitudinal movement of the frame along the pipe while testing the pipe.

10. The method of claim 9 which further comprises the steps of sensing the approach of the end of the pipe and providing a constraint on downward movement of the transducer when the end is neared to insure accurate testing of the entire length of the pipe.

11. The method of claim 10 wherein the constraint is provided by a coupling between the frame and the transducer which restricts movement toward the center of the pipe while permitting movement of said transducer away from the center in response to variations of the pipe shape.

12. Apparatus for maintaining a transducer in contact with a pipe comprising:
    (a) means for positioning a pipe in relation to a frame, said frame movable along the length of the pipe;
    (b) means for connecting a transducer to the frame which restricts translational transducer movement relative to the frame to two translational directions orthogonal to frame movement while said transducer rests on the pipe while substantially preventing transducer movement about the pipe's circumference; and
    (c) means for providing relative longitudinal movement of the frame and the pipe.

13. A method for pipe inspection comprising the steps of:

(a) positioning the pipe beneath a frame, said frame moveable along the length of pipe;

(b) coupling a test head to said frame to allow the test head to rest on the pipe; said test head including one or more transducers ultrasonically coupled to said pipe;

(c) moving the frame and attached test head along the pipe to scan the pipe for flaws;

(d) sensing the approach of the end of the pipe; and (e) preventing downward movement of said test head away from said frame after the end of the pipe has been reached by providing an additional coupling between test head and frame.

14. The method of claim 13 wherein a coupling between test head and frame comprises a universal joint means to allow up and down and side to side movement of the test head and wherein the preventing step comprises retracting a carriage mounted to the frame away from the pipe to provide contact between a carriage surface and a support member coupled to the test head.

15. The method of claim 14 wherein the side to side movement of the support member is limited by contact with the carriage surface in a way to keep the test head from moving too great an extent about the pipe surface.

16. A pipe inspection system comprising:

(a) support means for positioning a pipe at an inspection station;

(b) a beam mounted frame positioned above the inspection station and movable along the pipe in a direction parallel to the pipe and including a box-like structure movable toward and away from said pipe to accommodate pipe of different diameter;

(c) carriage means mounted to the frame and coupled to the frame by a double acting pneumatic drive for movement toward and away from the pipe and further coupled to said frame by a positioning mechanism which limits carriage movement toward said pipe and maintains said carriage in an intermediate scanning position;

(d) a test head coupled to said frame by a universal joint mechanism which allows up and down and side to side movement of said test head in relation to said pipe and including a plurality of rollers which roll along the length of the pipe; said test head couplable to said carriage by a pair of vertically extending rods which contact a surface of said carriage through a ball support means in both the intermediate scanning position and in a position where the test head is retracted away from said pipe by said pneumatic drive;

(e) ultrasonic transducer means rotatably connected to the test head and contacting said pipe in the intermediate scanning and in a fully extended scanning position; said transducer operative to scan the pipe length for flaws or irregularities; and (f) sensor means coupled to the test head for sensing the position of said test head in relation to the pipe length and generating signals for controlling actuation of said drive to position the test head and transducers in said fully retracted, fully extended and intermediate scanning positions with said transducer in contact with said pipe in the fully extended and intermediate scanning positions.

17. The system of claim 16 wherein a plurality of test head rollers rest on the pipe and are positioned on either side of a vertical plane extending through the pipe center when the test head is in a scanning position.

18. A process for scanning along the length of a pipe for flaws comprising the steps of:

(a) coupling a transducer test head to a frame to allow relative movement between test head and frame;

(b) positioning the frame above a pipe to be tested to allow up and down movement of said test head in relation to said frame as the test head is supported by the pipe;

(c) moving the frame and test head along the pipe to scan for flaws along the pipe; and (d) limiting downward movement of the test head during a portion of the scan.

19. A pipe inspection system comprising:

(a) support means for positioning a pipe at an inspection station;

(b) an ultrasonic transducer for examining the pipe for defects;

(c) mounting means connected to the transducer for positioning the transducer in relation to the pipe, said mounting means including:

(i) a frame positioned near the pipe and movable in a direction perpendicular to the path of pipe travel;

(ii) a test head mechanism coupled to the frame and positionable on the pipe; said test head rotatably coupled to the transducer;

(iii) universal joint means connected to said test head for limiting test head movement to two degrees of translational movement and coupled to the frame, and (iv) positioning means connected to frame and couplable to the test head for impeding movement of the transducer in a vertical direction as the transducer nears the pipe end;

(d) drive means for providing relative longitudinal movement between the transducer and the pipe, and (e) said mounting means maintaining ultrasonic coupling between the pipe and the transducer during said movement along the entire length of the pipe while limiting tangential movement of the transducer about the pipe circumference.

20. The apparatus of claim 19, which further comprises a carriage means supported within the frame for vertical movement relative to the frame and couplable to the test head, said positioning means being connected between the frame and carriage means and operative to position said carriage with the frame during selected intervals of pipe testing.

21. The apparatus of claim 20, which further comprises a pneumatic cylinder connecting the frame to the carriage to provide vertical movement to the carriage.

22. The apparatus of claim 21, which further comprises ball support means connected to the test head and positioned to contact a surface of the carriage means when the carriage means is moved away from the pipe by combined action of the positioning means and the pneumatic cylinder.

23. The apparatus of claim 21, which further comprises sensor means for sensing the position of the transducer along the pipe for actuating the cylinder in response to said testing.

24. A method for maintaining a transducer in contact with a pipe comprising the steps of;

(a) positioning a pipe in relation to a frame, said frame being movable along the length of the pipe;

(b) connecting a transducer to the frame with a universal joint mechanism which allows the transducer to move in two directions orthogonal to a direction transverse to frame movement while said transducer rests on the pipe;
(c) providing relative longitudinal movement of the frame along the pipe while testing the pipe;
(d) sensing the approach of the end of the pipe, and
(e) providing a constraint on downward movement of the transducer when the pipe end is neared to insure accurate testing of the entire length of the pipe.

25. The method of claim 24, wherein the step of providing the constraint is executed by a coupling between frame and transducer which restricts movement toward the center of the pipe while permitting movement of said transducer away from the center in response to variation of the pipe shape.

26. A pipe inspection system comprising:
(a) support structure for positioning a pipe at inspection station;
(b) an ultrasonic transducer for examining the pipe for defects;
(c) mounting apparatus connected to the transducer for positioning the transducer for pipe inspection;
(d) drive structure for providing relative longitudinal movement between the transducer and the pipe, and
(e) said mounting apparatus including structure for flexibly facilitating transducer tracking of the pipe surface while limiting movement of the transducer about the pipe circumference independently of contact with the pipe surface.

27. A system for testing a pipe workpiece, said system comprising:
(a) a frame movable relative to the pipe;
(b) an ultrasonic transducer for examining the pipe, and
(c) coupling structure interposed between the frame and the transducer for supporting the transducer for said examination, said coupling structure comprising two series coupled universal joints.

28. A pipe inspection system comprising:
(a) structure for supporting the pipe at an inspection station;
(b) a frame longitudinally movable with respect to the pipe;
(c) a transducer for examining the pipe;
(d) apparatus for coupling the transducer to the frame, said coupling apparatus comprising a universal joint mechanism spaced from the transducer longitudinally with respect to the pipe axis.

29. Apparatus for testing a pipe at an inspection station, said apparatus comprising:
(a) a frame longitudinally movable relative to the pipe;
(b) a test head;
(c) coupling structure interposed between the test head and frame;
(d) a testing transducer coupled to the test head;
(e) said coupling structure including apparatus for constraining test head movement to:
(i) primarily translational movement in two orthogonal directions, and
(ii) two primarily rotational degrees of freedom about two orthogonal axes, while substantially preventing rotation of the test head about any axis parallel to the pipe axis.

* * * * *